(12) United States Patent
Suzuki et al.

(10) Patent No.: US 6,638,759 B2
(45) Date of Patent: Oct. 28, 2003

(54) PROCESS FOR PREPARATION OF OPTICALLY ACTIVE 1,2-DIOLS BY CULTIVATING MICROORGANISMS

(75) Inventors: Toshio Suzuki, Osaka (JP); Hideaki Idogaki, Osaka (JP); Atsushi Nakagawa, Osaka (JP)

(73) Assignee: Daiso Co., Ltd., Osaka-fu (JP)

( * ) Notice: Subject to any disclaimer, the term of this patent is extended or adjusted under 35 U.S.C. 154(b) by 29 days.

(21) Appl. No.: 09/892,743

(22) Filed: Jun. 28, 2001

(65) Prior Publication Data
US 2002/0019034 A1 Feb. 14, 2002

(30) Foreign Application Priority Data

Jun. 28, 2000 (JP) ........................................ 2000-194316

(51) Int. Cl.$^7$ ................................................. G12P 7/18
(52) U.S. Cl. ...................... 435/280; 435/158; 435/170; 435/252.1
(58) Field of Search ................................ 435/280, 158, 435/170, 252.1

(56) References Cited

FOREIGN PATENT DOCUMENTS

| EP | 0 435 551 | 7/1991 |
| JP | 4-73999 | 11/1992 |
| JP | 6-209781 | 8/1994 |
| JP | 7-147993 | 6/1995 |

OTHER PUBLICATIONS

The ATCC Catalogue of Bacteria, 1996, p. 26.*

Lee, L., et al. "Preparation of Optically Active 1,2–Diols and α–Hydroxy Ketones Using Glycerol Dehydrogenase as Catalyst: Limits to Enzyme–Catalyzed Synthesis due to Noncompetitive and Mixed Inhibition by Product", J. Org. Chem., vol. 51 (1986), pp. 25–36.

Suzuki, T., et al. "A novel generation of optically active 1,2–diols from the racemates by using halohydrin dehydro–dehalogenase", Tetrahedron: Asymmetry, vol. 5, No. 2 (1994), pp. 239–246.

Suzuki, T., et al. "Microbial Production of Optically Active 1,2–Diols Using Resting Cells of Alcaligenes sp. DS–S–7G", Journal of Fermentation and Bioengineering, vol. 78, No. 2 (1994), pp. 194–196.

Suzuki, T., et al. "A Novel Method for the Generation of (R)– and (S)–3–chloro–1,2–propanediol by Stereospecific Dehalogenating Bacteria and Their Use in the Preparation of (R)– and (S)–glycidol", Bioorganic and Medicinal Chemistry Letters, vol. 1, No. 7 (1991), pp. 343–346.

Naoya et al., "Optically active chlorohydrins as chiral C3 and C4 building units: Microbial resolution and synthetic applications", Database Biosis 'Online! Biosciences Information Service, Phildelphia, PA, US; 1998, Database accession No. PREV199800490955, XP002190671.

* cited by examiner

Primary Examiner—Irene Marx
(74) Attorney, Agent, or Firm—Wenderoth, Lind & Ponack, L.L.P.

(57) ABSTRACT

A process for preparation of an optically active 1,2-diol compound of the following formula:

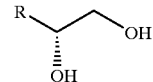

wherein R is alkyl group, hydroxy substituted alkyl group, or alkenyl group, which comprises reacting a corresponding racemic 1,2-diol compound with a strain belonging to the genus Alcaligenes which is being cultivated under aeration.

3 Claims, No Drawings

PROCESS FOR PREPARATION OF OPTICALLY ACTIVE 1,2-DIOLS BY CULTIVATING MICROORGANISMS

BACKGROUND OF THE INVENTION

The present invention relates to a process for preparation of optically active 1,2-diols by cultivating microorganisms belonging to the genus Alcaligenes, which 1,2-diols can be chiral building blocks and their intermediates useful for synthesis of optically active compounds such as pharmaceuticals, agrochemicals, physiological active compounds and ferroelectric liquid crystals.

PRIOR ART

In regard to a chemical method for preparation of optically active 1,2-diols, a method by stereoselective hydrolysis of an epoxide compound such as propylene oxide using Co(III)-salene catalyst and by converting it into a remaining optically active epoxide and a produced optically active diol was already reported by Jacobsen et al. (M. Tokunaga et al., Science, 277, 936–938 (1997)).

However, depending on a substrate, the optical purity of a 1,2-diol compound produced is low and the method needs expensive catalyst and therefore, the method is not economical.

As to an enzymatic method, a process of (R)-1,2-propanediol and (R)-1,2-butanediol, respectively from 1-hydroxy-2-propanone and 1-hydroxy-2-butanone by reduction with glycerol dehydrogenase by Lee and Whitesides (Journal of Organic Chemistry, Vol. 51, pp. 25–36 (1986)) and a process of an optically active 1,2-diol by using an oxidative dehalogenating enzyme (halohydrin dehydrodehalogenase; abbreviated as HDDase) by Suzuki (Tetrahedron/asymmetry, vol.5, 239–246 (1994), Japanese Patent Publication A 7-1479939) were reported.

Furthermore, as to a method using cells of microorganisms as catalyst, a process of a (S)-1,2-diol by reacting resting cells of microorganisms to a 1-hydroxy-2-ketone compound was known (Japanese Patent Publication A 1-320988). As to a process of a (R)-1,2-diol, an optical resolution method of (R)-1,2,4-butanetriol from racemic 1,2,4-butanetriol was known (Japanese Patent Publication A 6-209781).

However, in these enzymatic methods and methods by resting cells of microorganisms, the enzymes or the resting cells of microorganisms to react with a racemic 1,2-diol have to be separately prepared and then have to be subjected to the optical resolution reaction. Namely, as to the enzymatic reaction, the enzyme has to be extracted from the microorganisms by mechanically disruptive procedure etc. As to the method by the resting cells of microorganisms, the procedure of cultivation of the microorganisms and the procedure of the optical resolution are separately carried out and therefore, it takes extra time and procedure. In addition, when the resolution reaction proceeds with the oxidative- and reductive-degradative reaction, it is necessary to add co-enzyme and an electron acceptor to this reaction system and therefore, in view of the recycle of the reaction the enzymatic process is not efficient.

Thus, it was desired to develop the economical and simple process for preparation of optically active 1,2-diol compounds with highly optical purity.

The present inventors extensively engaged in the development of the process and led to completion of the present invention.

DETAILED DESCRIPTION OF THE INVENTION

The present invention relates to an improved process, namely to an efficiently and practically improved method of the above mentioned process for optically active 1,2-diol compounds by the enzymatic method using halohydrin dehydro-dehalogenase (HDDase)(Tetrahedron/asymmetry, vol. 5, 239–246(1994), Japanese Patent Publication A 7-147993).

Namely based on chemical and enzymatic property of the enzyme (HDDase) participating in the above reaction, by conjugating effective reproduction system of co-enzyme of living microorganisms, an economical and simple process for preparation of optically active 1,2-diol compounds of the formula [2] shown below was developed by the present inventors.

Furthermore, the present inventors found that in case of racemic 1,2,4-butanetriol as a substrate being subjected to the optical resolution by the method of the present invention, (S)-2,4-dihydroxybutyric acid is obtainable together with (R)-1,2,4-butanetriol.

The process of optically active 2,4-dihydroxybutyric acid from racemic 2-hydroxy-γ-butyrolactone by the optical resolution method using lactoinase was already reported (Japanese Patent Publication A 9-308497), but it is the first time to report the production of optically active 2,4-dihydroxybutyric acid together with an optically active 1,2-diol compound.

In regard to the known enzymatic method by HDDase mentioned above, in case of degradative elimination of an optically active 1,2-diol compound from a racemic 1,2-diol compound by the stereoselective oxidative degradation reaction, it is necessary to add expensive nicotinamide adenine dinucleotide (abbreviated as $NAD^+$) or an artificial electron acceptor as co-enzyme to the reaction mixture separately.

Therefore, in the enzymatic method by HDDase, the reproduction of co-enzyme becomes rate-determination or reaction controlling factor (Tetrahedron/asymmetry, vol.5, 239–246(1994), J. Ferment. Bioeng., vol. 78, 194–196 (1994)) and the method is not practical.

The present invention relates to an economical and practical process for preparation of an optically active 1,2-diol compound [2] shown below which is characterized in recovering said compound remaining by oxidative degradative eliminating the other optically active 1,2-diol compound or converting it into a carboxylic acid from a racemic 1,2-diol compound by repeatedly using $NAD^+$ produced in the growing microorganisms under the aeration, without addition of $NAD^+$ or an artificial electron acceptor necessary as co-enzyme to the reaction mixture separately.

As mentioned above, the method of the present invention is fundamentally different from the known enzymatic method by purified HDDase and the known method by resting cells of microorganisms (Tetrahedron/asymmetry, vol. 5, 239–246(1994), J. Ferment. Bioeng., vol. 78, 194–196(1994)).

The present invention relates to a process for preparation of an optically active 1,2-diol compound of the following formula [2]:

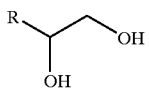

wherein R is alkyl group, hydroxy substituted alkyl group, or alkenyl group, which comprises reacting a racemic 1,2-diol compound of the following formula [1]:

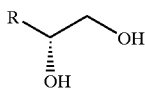

wherein R is the same as defined,
with a strain belonging to the genus Alcaligenes which is being cultivated under aeration, and recovering said optically active 1,2-diol compound from said culture broth.

In addition, the present invention also relates to, when racemic 1,2,4-butanetriol is used as a substrate (R is hydroxyethyl group in the formula [2]), a process for preparation of (R)-1,2,4-butanetriol and (S)-2,4-dihydroxybutyric acid by reacting said substrate with a strain belonging to the genus Alcaligenes which is being cultivated under aeration.

This reaction is shown as follows:

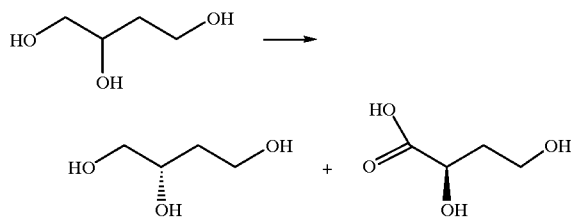

DETAILED DESCRIPTION OF THE PREFERRED EMBODIMENTS

The present inventors developed the economical and practical process for an optically active 1,2-diol compound [2] from a racemic 1,2-diol compound [1] by reacting said racemate with microorganisms belonging to the genus Alcaligenes which are being aerobically cultivated in a nutrient culture medium consisting of peptone or yeast extract as a source of nitrogen and 3-chloropropanediol or gluconic acid as a source of carbon, while making $NDA^+$ reproduce in the said microorganisms without introducing $NDA^+$ from outside.

The microorganisms used in the present invention are ones producable halohydrin dehydro-dehalogenase (HDDase), for example Alcaligenes sp. DS-S-7G (FERM BP-3098), Alcaligenes sp. DS-S-8S (FERM BP-3099) and Alcaligenes sp. DS-S-1C (FERM BP-3100) belonging to the genus Alcaligenes, which were isolated from the soil by the present inventors and deposited on Nov. 15, 1989 to the National Institute of Bioscience and Human-Technology Agency of Industrial Science and Technology, Japan under Budapest Treaty with the above accession number, respectively.

The above strains were selected from the soil indexing the ability degrading and assimilating (R)-3-chloro-1,2-propanediol, and can grow in the minimum broth containing a basic culture medium consisting of a small amount of phosphate and magnesium sulfate and a small amount of metallic salts containing inorganic nitrogen source such as ammonium sulfate, and (R)-3-chloro-1,2-propanediol as a single source of carbon (Japanese Patent Publication B 4-73999, Bioorg. Med. Chem. Lett., 1, 343–346 (1991)).

The culture medium for cultivation of the microorganisms used in the present invention is not limited as long as the microorganisms can grow in the culture medium.

For example, there are illustrated alcohols such as glycerol, a racemic 3-halogeno-1,2-propanediol or a (R)-3-halogeno-1,2-propanediol, organic acids such as acetic acid, citric acid, malic acid, maleic acid, fumalic acid, gluconic acid, a salt thereof or a mixture thereof as a source of carbon, and inorganic nitrogen compounds such as ammonium sulfate, ammonium nitrate or ammonium phosphate, and organic nitrogen compounds such as urea, peptone, casein, yeast extract, meat extract, corn steep liquor or a mixture thereof as a source of nitrogen. Further, inorganic salts such as a phosphoric acid salt, a magnesium salt, a potassium salt, a manganese salt, an iron salt, a zinc salt, a cooper salt, or if suitable, vitamins may be used. Furthermore, in order to induce high HDDase activity in case of cultivation of the above strains in the above medium or a nutrient medium such as a peptone medium or a bouillon medium, a racemic 3-halogeno-1,2-propanediol or a (R)-3-halogeno-1,2-propanediol may be added. One of the preferable embodiments is to cultivate in a complete synthetic medium containing a racemic 3-halogeno-1,2-propanediol or a (R)-3-halogeno-1,2-propanediol as a single source of carbon.

The microorganisms used in the present invention can be cultivated in the usual manner, for example at pH 4–9, preferably 4.5–8.5, at the temperature of 20–45° C., preferably 25–37° C. and aerobically for 10–96 hours.

Preferable substrates used in the present invention include racemates of 1,2,4-butanetriol, 1,2-propanediol, 1,2-butanediol, 1,2-pentanediol, 1,2-hexanediol, 1,2-dihydroxy-3-butene and 1,2-dihydroxy-5-hexene.

As mentioned above, when the procedure of the present invention is carried out using racemic 1,2,4-butanetriol as a substrate, there are obtainable remaining (R)-1,2,4-butanetriol together with (S)-2,4-dihydroxybutyric acid. The separation of both compounds is carried out with column chromatograph by ion exchange resin or silica gel, or after condensing the culture broth under neutral conditions, by substitution of the solvent with an alcohol, and is carried out by precipitating 2,4-dihydroxybutyric acid as its salt and leaving 1,2,4-butanetriol in the supernatant.

The reaction by the cultivation is carried out at a temperature of 20–45° C., preferably 25–37° C., at pH of 4–9, preferably 4.5–8.5. The concentration of the substrate in the reaction medium is preferably 0.1–15% (v/v). The substrate may be added to the culture medium at once in the initial step or dividedly.

The reaction is usually carried out under aerobical shaking or agitation, and the reaction is preferably completed in 24–120 hours, depending on the concentration of the substrate or the amount of the microorganisms. When the residual amount of the substrate becomes 50% comparing with the initial concentration of the substrate by gas chromatography, the reaction is preferably quenched.

When pH in the reaction medium decreases with a progress of the reaction by an acid produced by oxidative degradation of the substrate, the pH value may be adjusted to optimum pH by addition of aqueous sodium hydroxide, aqueous ammonia, or an aqueous solution of alkali carbonates such as calcium carbonate.

Thus obtained optically active 1,2-diol compound remaining in the reaction mixture can be recovered and purified with the conventional method.

For example, after removal of cells of the microorganisms from the reaction medium, the supernatant is condensed by an evaporator, extracted with ethyl acetate, dried on anhydrous magnesium sulfate, and the solvent is evaporated in vacuo to give an optically active 1,2-diol compound in syrup. Further the product may be purified by distillation or column chromatography with silica gel.

The present invention is explained in detail with following examples, but the scope of the present invention should be not limited by these examples. Percentage (%) in the examples means the percentage (w/v) unless specific indication.

EXAMPLE 1

A medium (1L) consisting of polypeptone, yeast extract and gluconic acid, respectively containing 1%(w/v) was poured into ajar fermentor (2L) and was sterilized at 121° C. for 15 minutes. To the medium was added racemic 1,2,4-butanetriol which was separately sterilized at 121° C. for 15 minutes in the concentration of 5% (w/v) to prepare a nutrient medium.

Previously, a loopful of Alcaligenes sp. DS-S-7G was cultivated under shaking in the semi-synthetic medium (100 ml, pH 7.2) containing peptone, yeast extract and racemic 3-chloro-1,2-propanediol, respectively containing 1.0% at 30° C. for 20 hours and then 20 ml of the culture medium was sterilely inoculated to the above nutrient medium. The culture medium was cultivated at 30° C., at 500 rpm for about 24 hours under aerobical agitation at aeration rate of 500 ml/min. The measurement of pH and its control was made by a pH meter connected and its pH was adjusted to 6.5 with 5N sodium hydroxide.

After the cultivation was completed, 1,2,4-butanetriol remaining in the reaction culture medium was analyzed by gas chromatography (column support: PEG20M, 60–80 mesh) and the remaining ratio was 49.2%. Simultaneously the formation of 2,4-dihydroxybutyric acid was confirmed. Then the culture medium was subjected to centrifugation to remove the cells, condensed to about 40 ml and extracted with three times as much ethanol (120 ml).

There were obtained an alcohol solution of 1,2,4-butanetriol and precipitate of sodium 2,4-dihydroxybutyrate. The ethanol layer was dried on anhydrous magnesium sulfate and the solvent was removed in vacuo to give 1,2,4-butanetriol (21.6 g) in syrup. On the other hand the precipitate was collected and again washed with ethanol and the solvent was removed in vacuo to give crude sodium 2,4-dihydroxybutyrate (5.6 g).

The identification of the products was carried out by GC/MS and productions of 1,2,4-butanetriol and sodium 2,4-dihydroxybutyrate were confirmed in the reaction culture broth. The measurement of optical purity of 1,2,4-butanetriol in the syrup was carried out by subjecting to gas chromatography with Capillary column: astec CHRALDEX G-TA (inner diameter; 0.25×30) after it was trifluoroacetylated with trifluoroacetic acid anhydride.

As a result, the optical purity of 1,2,4-butanetriol recovered was more than 98% ee in (R) isomer. Conditions on the above gas chromatography analysis were as follows:
Retention time of R isomer; 39.3 min., S isomer; 40.6 min.
Analysis temperature: column temp. (100° C.; inject temperature 200° C., carrier gas: nitrogen (flow 1 ml/min),
Detection: FID sprit ratio: 100/1

On the other hand 2,4-dihydroxybutyric acid in the culture broth was refluxed with 0.5M HCl at 200° C. for 2 hours to convert 2-hydroxy-γ-butyrolactone (JP 09308497). The reaction mixture was extracted with ethyl acetate and the solvent was removed to give crude 2-hydroxy-γ-butyrolactone. Its chemical purity was 80% by the measurement with gas chromatography (column support: PEG20M, 60–80 mesh). Its specific rotation was $[\alpha]_D = -51.9°$ (25° C., c=1.132, $CHCl_3$) and its steric conformation was (S) isomer. Value described in the literature: $[\alpha]_D = -65.2°$ (25° C., c=1.15, $CHCl_3$)

EXAMPLE 2-2

In the same manner as above Example 1, the optical resolutions were carried out by using following substrates instead of 1,2,4-butanetriol, and by using DS-S-8S or DS-S-1C instead of DS-S-7G.

| Ex. No. | Substrate | Conc. of substrate % (w/v) | Yield (g) | Optical purity (% ee) |
|---|---|---|---|---|
| Strain: DS-S-7G | | | | |
| 2 | 1,2-Butanediol | 5 | 20.1 | >98 (R) |
| 3 | 1,2-Pentanediol | 5 | 20.2 | >98 (R) |
| 4 | 1,2-Hexanediol | 5 | 20.5 | >98 (R) |
| 5 | 1,2-Dihydroxy-3-butene | 1 | 4.3 | >98 (R) |
| 6 | 1,2-Dihydroxy-5-hexene | 1 | 4.1 | >98 (R) |
| 7 | 1,2-Propanediol | 5 | 13.5 | >98 (R) |
| Strain: DS-S-8S | | | | |
| 8 | 1,2,4-Butanetriol | 5 | 21.3 (5.4)* | >98 (R) (>80 (S))* |
| 9 | 1,2-Butanediol | 5 | 20.1 | >98 (R) |
| 10 | 1,2-Pentanediol | 5 | 20.6 | >98 (R) |
| 11 | 1,2-Hexanediol | 5 | 21.5 | >98 (R) |
| 12 | 1,2-Dihydroxy-3-butene | 1 | 4.1 | >98 (R) |
| 13 | 1,2-Dihydroxy-5-hexene | 1 | 4.2 | >98 (R) |
| 14 | 1,2-Propanediol | 5 | 12.9 | >98 (R) |
| Strain: DS-S-1C | | | | |
| 15 | 1,2,4-Butanetriol | 5 | 20.3 (5.1)* | >98 (R) (>80 (S))* |
| 16 | 1,2-Butanediol | 5 | 21.3 | >98 (R) |
| 17 | 1,2-Pentanediol | 5 | 20.4 | >98 (R) |
| 18 | 1,2-Hexanediol | 5 | 20.4 | >98 (R) |
| 19 | 1,2-Dihydroxy-3-butene | 1 | 4.1 | >98 (R) |
| 20 | 1,2-Dihydroxy-5-hexene | 1 | 4.2 | >98 (R) |
| 21 | 1,2-Propanediol | 5 | 12.5 | >98 (R) |

Note:
*The values mean ones corresponding to 2,4-dihydroxybutyric acid.

Effect of the Invention

According to the present invention, by using the aerobical culture broths of Alcaligenes sp. DS-S-7G, Alcaligenes DS-S-8S and Alcaligenes sp. DS-S-1C belonging to the genus Alcaligenes, a (R)-1,2-diol compound can be economically and in simple produced from a racemic 1,2-diol compound by oxidative degradative eliminating the other optical isomer. And when racemic 1,2,4-butanetriol is used as a substrate, (R) 1,2,4-butanetriol and (S) dihydroxybutyric acid are prepared.

What is claimed is:
1. A process for preparation of (R)-1,2,4-butanetriol and (S)-2,4-dihydroxybutyric acid which comprises reacting racemic 1,2,4-butanetriol with a strain belonging to the genus Alcaligenes selected from the group consisting of Alcaligenes sp. DS-S-7G (FERMBP-3098), Alcaligenes sp. DS-S-8S (FERM BP-3099) and Alcaligenes sp. DS-S-1C (FERM BP-3100) which is being cultivated under aeration, and recovering said (R)-1,2,4-butanetriol and said (S)-2,4-dihydroxybutyric acid from the resultant culture broth.

2. A process for preparation of (S)-2,4-dihydroxybutyric acid which comprises reacting racemic 1,2,4-butanetriol with a strain belonging to the genus Alcaligenes selected from the group consisting of Alcaligenes sp. DS-S-7G (FERM BP-3098), Alcaligenes sp. DS-S-8S (FERM BP-3099) and Alcaligenes sp. DS-S-1C (FERM BP-3100) which is being cultivated under aeration, and recovering said (S)-2,4-dihydroxybutyric acid from the resultant culture broth.

3. A process for preparation of (R)-1,2,4-butanetriol which comprises reacting racemic 1,2,4-butanetriol with a strain belonging to the genus Alcaligenes selected from the group consisting ofAlcaligenes sp. DS-S-7G (FERM BP-3098), Alcaligenes sp. DS-S-8S (FERM BP-3099) and Alcaligenes sp. DS-S-1C (FERM BP-3100) which is being cultivated under aeration, and recovering said (R)-1,2,4-butanetriol from the resultant culture broth.

* * * * *